United States Patent
Ogawa et al.

(10) Patent No.: US 11,141,887 B2
(45) Date of Patent: Oct. 12, 2021

(54) PRODUCTION METHOD OF MOLD HAVING RECESSED PATTERN, AND MANUFACTURING METHOD OF PATTERN SHEET

(71) Applicant: FUJIFILM Corporation, Tokyo (JP)

(72) Inventors: Shotaro Ogawa, Kanagawa (JP); Toshihiro Usa, Kanagawa (JP); Kenichiro Tamaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 486 days.

(21) Appl. No.: 16/175,850

(22) Filed: Oct. 31, 2018

(65) Prior Publication Data
US 2019/0070754 A1    Mar. 7, 2019

Related U.S. Application Data

(63) Continuation of application No. PCT/JP2017/015652, filed on Apr. 19, 2017.

(30) Foreign Application Priority Data

May 10, 2016 (JP) .............................. JP2016-094287

(51) Int. Cl.
*B29C 33/38* (2006.01)
*B29C 59/02* (2006.01)
(Continued)

(52) U.S. Cl.
CPC ..... *B29C 33/3807* (2013.01); *A61M 37/0015* (2013.01); *B29C 33/3842* (2013.01);
(Continued)

(58) Field of Classification Search
CPC . B29C 33/3807; B29C 33/3857; B29C 33/20; B29C 59/02; B29C 45/1742; B29C 45/2675
See application file for complete search history.

(56) References Cited

U.S. PATENT DOCUMENTS 6,474,976 B1 * 11/2002 Oami ..................... B29C 33/18
425/503
10,029,081 B2    7/2018 Che et al.
(Continued)

FOREIGN PATENT DOCUMENTS

DE    2927429        1/1981
DE    2927429 A1 *  1/1981 ............. B29C 43/12
(Continued)

OTHER PUBLICATIONS

"Office Action of Australia Counterpart Application," dated Jul. 27, 2019, p. 1-p. 3.
(Continued)

*Primary Examiner* — Jacob T Minskey
*Assistant Examiner* — Virak Nguon
(74) *Attorney, Agent, or Firm* — JCIPRNET

(57) ABSTRACT

Provided are a production method of a mold having a recessed pattern, and a manufacturing method of a pattern sheet having good accuracy and excellent productivity. The production method of a mold includes: a step of preparing an electroform having a protruding pattern and a mold having a first mold and a second mold forming a cavity; a step of fixing the electroform excluding an end portion of the electroform to the first mold; a clamping step of clamping the electroform excluding the end portion of the electroform and a region of the protruding pattern between the first mold and the second mold to form the cavity; and an injection step of filling the cavity with a resin.

9 Claims, 11 Drawing Sheets

(51) Int. Cl.
  *B29C 45/17* (2006.01)
  *B29C 45/37* (2006.01)
  *A61M 37/00* (2006.01)
  *B29L 31/00* (2006.01)
  *C25D 1/10* (2006.01)
  *B29C 33/40* (2006.01)
  *B29C 33/00* (2006.01)
  *B29C 33/20* (2006.01)

(52) U.S. Cl.
  CPC ...... *B29C 33/3857* (2013.01); *B29C 45/1742* (2013.01); *B29C 45/372* (2013.01); *B29C 59/02* (2013.01); *A61M 2037/0046* (2013.01); *A61M 2037/0053* (2013.01); *B29C 33/0011* (2013.01); *B29C 33/20* (2013.01); *B29C 33/405* (2013.01); *B29L 2031/756* (2013.01); *B29L 2031/7544* (2013.01); *C25D 1/10* (2013.01)

(56) References Cited

U.S. PATENT DOCUMENTS

| | | | |
|---|---|---|---|
| 2002/0053756 A1* | 5/2002 | Powell | B29C 33/424 264/313 |
| 2007/0191761 A1* | 8/2007 | Boone | B29C 33/3842 604/46 |
| 2008/0088066 A1* | 4/2008 | Ferguson | A61M 37/0015 264/443 |
| 2008/0251975 A1 | 10/2008 | Gallagher et al. | |
| 2011/0098651 A1* | 4/2011 | Falo, Jr. | A61L 31/06 604/173 |
| 2012/0258284 A1* | 10/2012 | Rendon | A61M 37/0015 428/156 |
| 2015/0238413 A1 | 8/2015 | Mochizuki et al. | |
| 2015/0238743 A1* | 8/2015 | Che | B32B 27/26 156/285 |
| 2016/0158514 A1 | 6/2016 | Stoeber et al. | |
| 2017/0312489 A1 | 11/2017 | Stoeber et al. | |
| 2019/0201674 A1 | 6/2019 | Stoeber et al. | |

FOREIGN PATENT DOCUMENTS

| | | | |
|---|---|---|---|
| DE | 4301654 | 7/1994 | |
| EP | 3357659 | 8/2018 | |
| JP | H1134120 | 2/1999 | |
| JP | 2010006010 | 1/2010 | |
| JP | 2010213845 | 9/2010 | |
| JP | 2013074924 | 4/2013 | |
| JP | 2013251301 | 12/2013 | |
| JP | 2015226649 | 12/2015 | |
| JP | 2015226649 A * | 12/2015 | ........ A61M 37/0015 |
| JP | 6000656 | 10/2016 | |
| JP | 6249885 | 12/2017 | |
| KR | 20070094218 | 9/2007 | |
| KR | 20140039713 | 4/2014 | |
| KR | 20160019944 | 2/2016 | |
| WO | 2011155035 | 12/2011 | |
| WO | 2014077242 | 5/2014 | |
| WO | 2014077243 | 5/2014 | |

OTHER PUBLICATIONS

Office Action of Japan Counterpart Application, with English translation thereof, dated Sep. 9, 2019, pp. 1-6.

"Search Report of Europe Counterpart Application", dated Apr. 1, 2019, p. 1-p. 7.

"Office Action of Australia Counterpart Application", dated Oct. 28, 2020, p. 1-p. 4.

"Written Opinion of the International Searching Authority (Form PCT/ISA/237) of PCT/JP2017/015652," dated Jul. 18, 2017, with English translation thereof, pp. 1-7.

"International Search Report (Form PCT/ISA/210) of PCT/JP2017/015652," dated Jul. 18, 2017, with English translation thereof, pp. 1-5.

"Office Action of Korea Counterpart Application," with English translation thereof, dated Jan. 21, 2020, p. 1-p. 14.

"Office Action of China Counterpart Application," dated Feb. 6, 2020, with English translation thereof, p. 1-p. 17.

* cited by examiner

PRODUCTION METHOD OF MOLD HAVING RECESSED PATTERN, AND MANUFACTURING METHOD OF PATTERN SHEET

CROSS-REFERENCE TO RELATED APPLICATIONS

The present application is a Continuation of PCT International Application No. PCT/JP2017/015652 filed on Apr. 19, 2017 claiming priority under 35 U.S.C. § 119(a) to Japanese Patent Application No. 2016-094287 filed on May 10, 2016. Each of the above applications is hereby expressly incorporated by reference, in their entirety, into the present application.

BACKGROUND OF THE INVENTION

1. Field of the Invention

The present invention relates to a production method of a mold having a recessed pattern, and a manufacturing method of a pattern sheet.

2. Description of the Related Art

In recent years, as a novel dosage form capable of injecting drugs such as insulin, vaccines, and human growth hormone (hGH) into the skin without pain, a microneedle array has been known. The microneedle array is an array of microneedles (also referred to as fine needles or small needles) which contain drugs and are biodegradable. By attaching this microneedle array to the skin, each microneedle pierces the skin, and these microneedles are absorbed in the skin such that the drugs contained in each microneedle can be administered into the skin. Microneedle arrays are also called percutaneous absorption sheets.

Various suggestions have been made as a manufacturing method of a microneedle array having a fine pattern as described above. JP2013-074924A discloses manufacturing a microneedle array by preparing a mold having a plurality of conical recesses, filling the recesses with a needle raw material, drying the filled raw material so as to solidify, and releasing the resultant from the mold.

SUMMARY OF THE INVENTION

In JP2013-074924A, it is disclosed that the mold having the plurality of conical recesses may be formed by injection molding in which molding is performed with a resin melted in a plate precursor. However, a specific configuration in a case of performing injection molding using an electroform is not disclosed.

The present invention has been made taking the above circumstances into consideration, and an object thereof is to provide a production method of a mold having a recessed pattern using an electroform, and a manufacturing method of a pattern sheet using the mold.

According to an aspect of the present invention, a production method of a mold having a recessed pattern comprises: a step of preparing an electroform having a protruding pattern and a mold having a first mold and a second mold; a step of fixing the electroform to the first mold; a clamping step of clamping the electroform excluding the end portion of the electroform and a region of the protruding pattern between the first mold and the second mold to form a cavity; and an injection step of filling the cavity with a resin.

Preferably, in the step of fixing the electroform to the first mold, the electroform is fixed to the first mold by at least one of vacuum adsorption or a magnetic force.

Preferably, the resin is any one of a thermosetting resin and a silicone resin.

Preferably, the electroform has a shape in which a thickness of a region of the end portion is larger than a thickness of a region excluding the region of the end portion.

Preferably, after the injection step, a releasing step of curing the resin in the cavity through heating, opening the first mold and the second mold, and releasing the cured resin from the electroform is further comprised.

Preferably, the electroform is circular in a plan view.

Preferably, a flat surface is formed on a side of the first mold to which the electroform is fixed, and a depression is formed on a cavity side of the second mold.

According to another aspect of the present invention, a manufacturing method of a pattern sheet comprises: a step of producing a mold having a recessed pattern by the production method of a mold having a recessed pattern described above; a supply step of supplying a polymer solution to the recessed pattern of the mold; a drying step of drying the polymer solution to form a polymer sheet; and a polymer sheet releasing step of releasing the polymer sheet from the mold.

Preferably, the polymer solution contains a water-soluble material.

According to the present invention, a mold can be produced using an electroform with good accuracy and excellent productivity. A pattern sheet can be manufactured using the mold.

DESCRIPTION OF THE PREFERRED EMBODIMENTS

Figure 1:
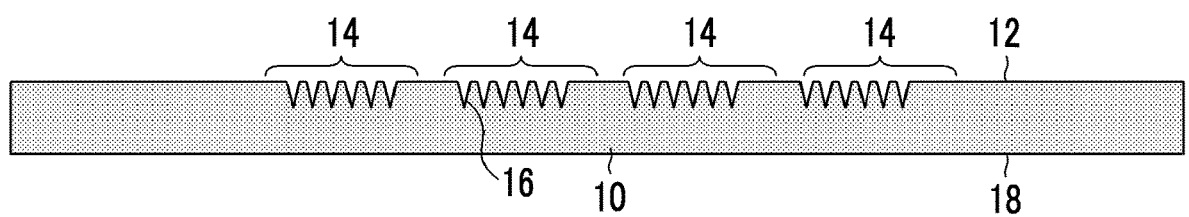
FIG. 1 is a process diagram illustrating a production method of an electroform.

Hereinafter, preferred embodiments of the present invention will be described with reference to the accompanying drawings. The present invention is described by the following preferred embodiments. Modifications can be made by various methods without departing from the scope of the present invention, and other embodiments than this embodiment can also be used. Therefore, all modifications within the scope of the present invention are included in the appended claims.

Here, in the figures, like elements having similar functions are denoted by like reference numerals. In addition, in this specification, in a case where a numerical value range is expressed using "to", the numerical value range includes the numerical values of the upper limit and the lower limit indicated by "to".

<Production Method of Mold>

An embodiment of the present invention will be described with reference to FIGS. 1 to 14. A production method of a mold of this embodiment includes: a step of preparing an electroform having a protruding pattern and a mold having a first mold and a second mold; a step of fixing the electroform excluding an end portion of the electroform to the first mold; a clamping step of clamping the electroform excluding the end portion of the electroform and a region of the protruding pattern between the first mold and the second mold in order to form a cavity; and an injection step of filling the cavity with a resin.

The electroform used for the production of the mold is prepared. For example, the electroform is produced based on process diagrams illustrated in FIGS. 1 to 4. As illustrated in FIG. 1, a master model 10 for producing the electroform is prepared. On a first surface 12 of the master model 10, a recessed pattern 14 which is an inverted shape of the electroform having a protruding pattern to be produced is formed. The recessed pattern 14 is a state in which a plurality of recesses 16 are arranged in an array. The recesses 16 are produced according to the shape of the electroform to be produced. In this embodiment, the recess 16 has a shape tapered from the first surface 12 toward a second surface 18. Example of the tapered shape may include a cone shape, a combination of a column shape and a cone shape, and a combination of a frustum shape and a cone shape. In this embodiment, a plurality of the recessed patterns 14 are formed on the first surface 12 of the master model 10.

Figure 2:
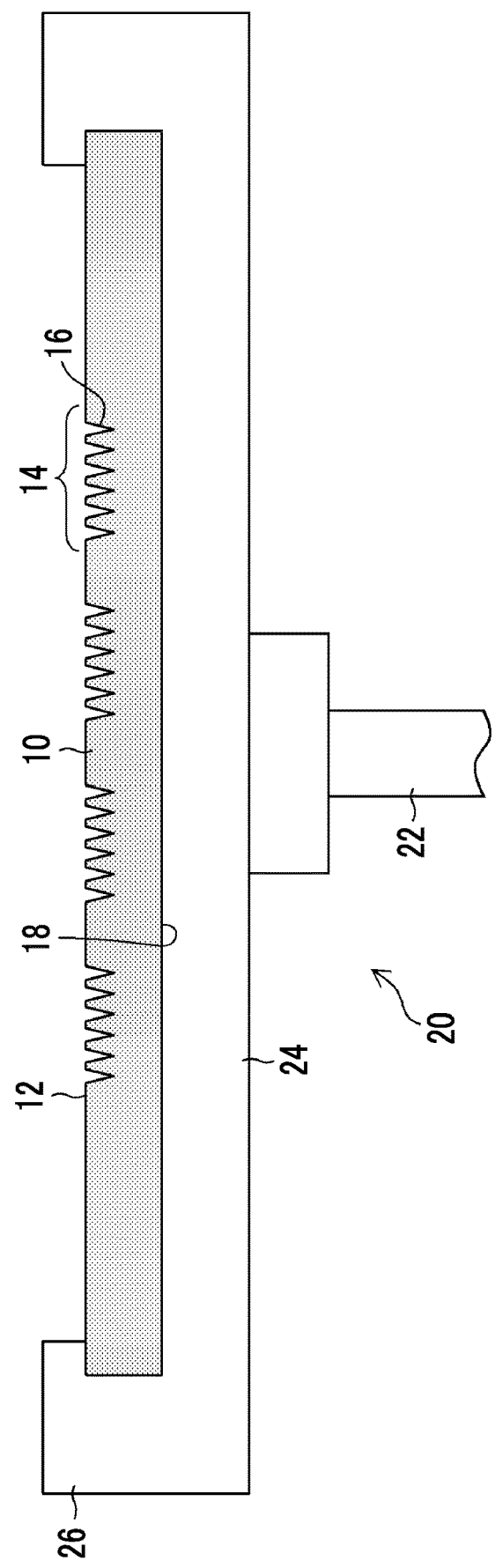
FIG. 2 is a process diagram illustrating the production method of an electroform.

As illustrated in FIG. 2, the master model 10 is fixed to a cathode 20 used in an electroforming treatment. The cathode 20 comprises at least a shaft 22 and a cathode plate 24. The master model 10 is fixed to the cathode plate 24 at a position where the second surface 18 of the master model 10 and the cathode plate 24 face each other.

In a case where the master model 10 is made of a resin material, a conduction treatment is performed on the master model 10. A metal film (for example, nickel) is formed on the first surface 12 of the master model 10 and the recessed patterns 14 by vapor deposition, sputtering, or the like. In order to supply a current from the cathode plate 24 to the metal film (not illustrated), a conductive ring 26 is provided at the outer peripheral portion of the master model 10. The shaft 22 and the cathode plate 24 are formed of a conductive member. Here, the electroforming treatment refers to a treatment method of depositing metal on the surface of the master model 10 by an electroplating method.

Figure 3:
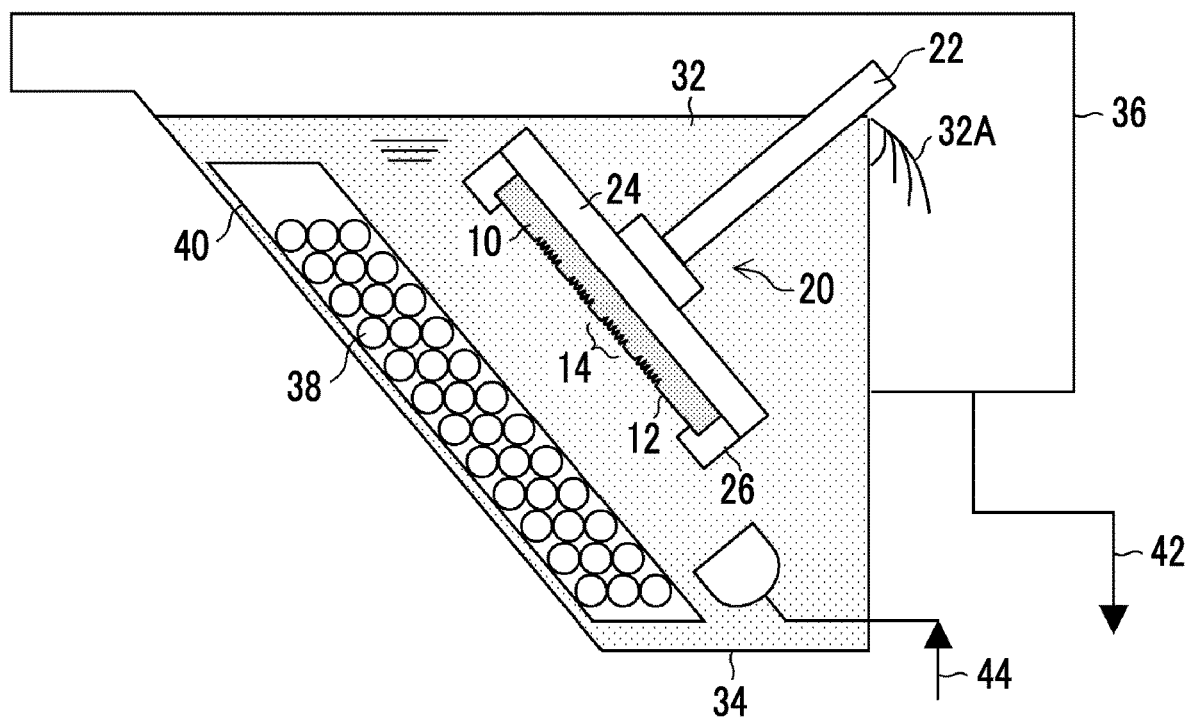
FIG. 3 is a process diagram illustrating the production method of an electroform.

As illustrated in FIG. 3, the master model 10 attached to the cathode 20 is immersed in an electroforming liquid 32. As illustrated in FIG. 3, an electroforming apparatus 30 for performing the electroforming treatment on the master model 10 comprises an electroforming tank 34 that holds the electroforming liquid 32, a drain tank 36 that receives the overflowing electroforming liquid 32A from the electroforming tank 34, and a titanium case 40 filled with Ni pellets 38. By immersing the cathode 20 having the master model 10 attached thereto in the electroforming liquid 32, the electroforming apparatus 30 operates. As the electroforming liquid 32, for example, a liquid in which 400 to 800 g/L of nickel sulfamate, 20 to 50 g/L of boric acid, and necessary additives such as a surfactant (for example, sodium lauryl sulfate) are mixed can be used. The temperature of the electroforming liquid 32 is preferably 25° C. to 60° C.

A drain pipe 42 is connected to the drain tank 36, and a supply pipe 44 is connected to the electroforming tank 34. The electroforming liquid 32 overflowing from the electroforming tank 34 to the drain tank 36 is recovered by the drain pipe 42, and the recovered electroforming liquid 32 is supplied from the supply pipe 44 to the electroforming tank 34. The master model 10 held by the cathode 20 is located at a position at which the first surface 12 on which the recessed patterns 14 are formed faces the titanium case 40 serving as an anode.

The cathode 20 is connected to a negative electrode, and a positive electrode is connected to the titanium case 40 serving as the anode. A direct current voltage is applied between the cathode 20 and the titanium case 40 while the master model 10 held by the cathode plate 24 is rotated about the shaft 22 at a rotational speed of 10 to 150 rpm. The Ni pellets 38 are melted such that a metal film adheres to the recessed patterns 14 of the master model 10 attached to the cathode 20.

Figure 4:
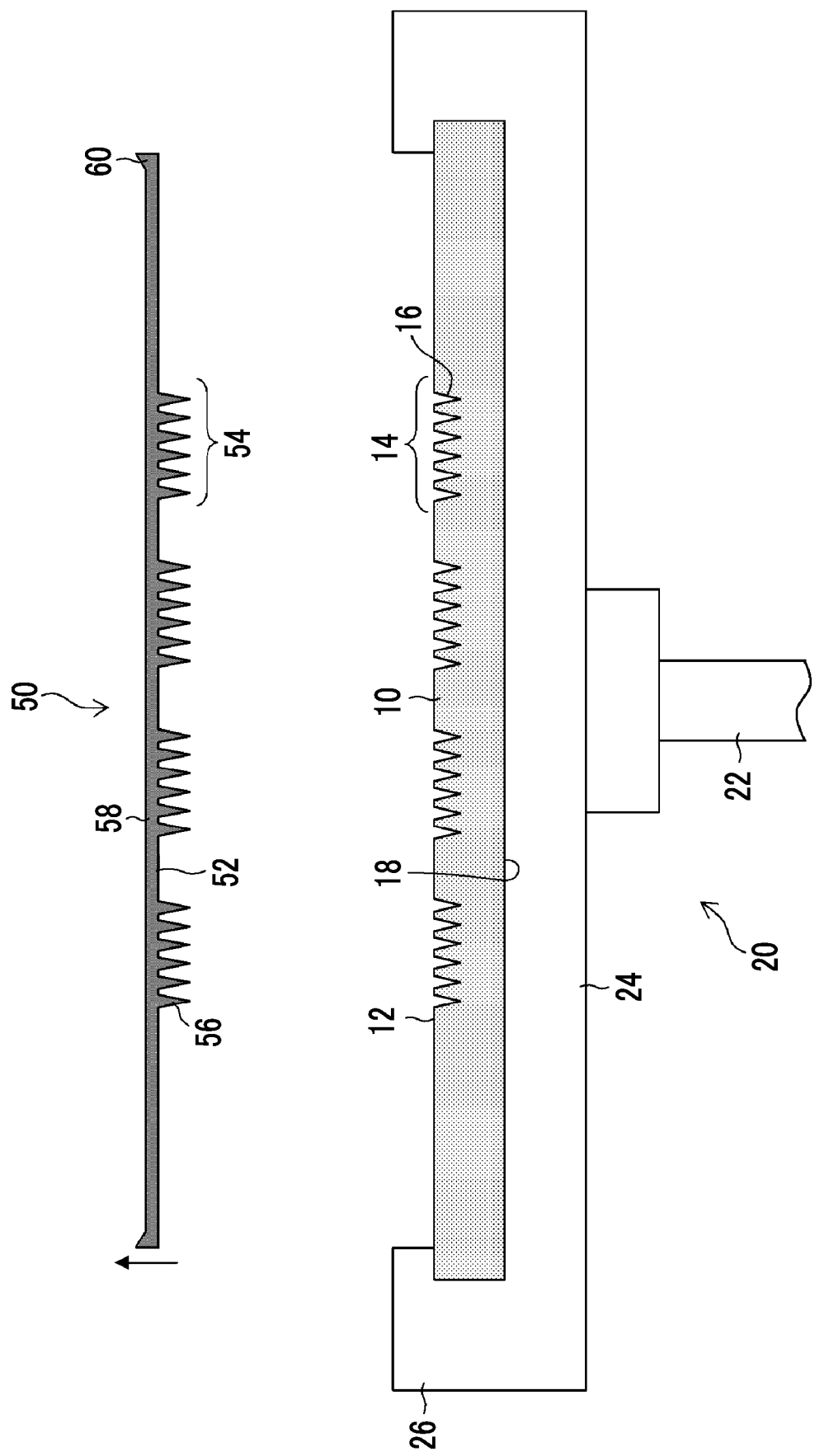
FIG. 4 is a process diagram illustrating the production method of an electroform.

As an electroform 50 made of the metal film is formed on the master model 10, as illustrated in FIG. 4, the cathode 20 to which the master model 10 is attached is taken out from the electroforming tank 34 (not illustrated). Next, the electroform 50 is peeled off from the master model 10. The electroform 50 having a first surface 52 and a second surface 58 and having protruding patterns 54 on the first surface 52 can be obtained. The protruding pattern 54 has an inverted shape of the recessed pattern 14 of the master model 10.

Figure 5:
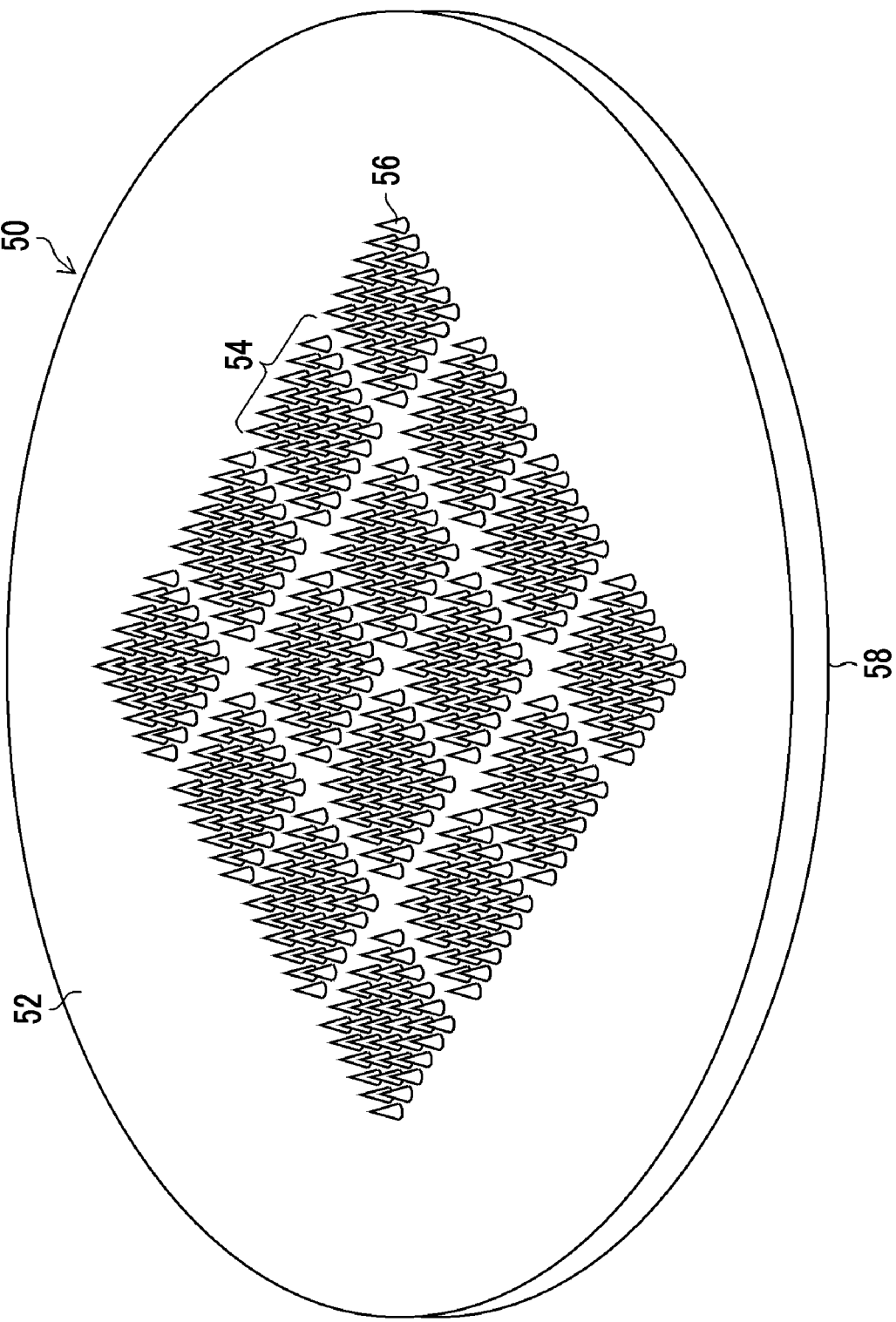
FIG. 5 is a perspective view of the electroform.

FIG. 5 is a perspective view of the electroform. As illustrated in FIG. 5, the protruding pattern 54 is a state in which a plurality of protrusions 56 are arranged in an array. In this embodiment, the protrusion 56 has a tapered shape protruding from the first surface 52. Examples of the tapered shape may include a cone shape, a combination of a column shape and a cone shape, and a combination of a frustum shape and a cone shape. In this embodiment, a plurality of the protruding patterns 54 are formed on the first surface 52 of the electroform 50. The height of the protrusion 56 is, for example, in a range of 0.2 mm or more and 2 mm or less, and preferably 0.3 mm or more and 1.5 mm or less. The height of the protrusion 56 is the distance from the first surface 52 to the tip of the protrusion 56.

In the electroforming treatment, in order to form a metal film of a uniform thickness on the first surface 12 of the master model 10, the electroform 50 is preferably circular in a plan view. The diameter of the electroform 50 is preferably 200 to 300 mm.

As described above, the electroform 50 is produced by supplying a current from the conductive ring 26. Therefore, as illustrated in FIG. 4, there may be cases where an end portion 60 of the electroform 50, which is in contact with the conductive ring 26, has different physical properties (for example, thickness and surface roughness) compared to the other portions of the electroform 50.

In a case where the electroform 50 has the end portion 60 having different physical properties, during injection molding using the electroform 50, there is concern about accuracy of a produced mold due to instable fixing of the electroform 50 and the like.

It is also conceivable to remove the end portion 60 having different physical properties from the electroform 50 by processing such as cutting. However, there is concern that the electroform 50 may be deformed due to the influence of the processing and thus the height uniformity and the like of the protruding pattern 54 may be damaged. In addition, there is also concern that the productivity may be reduced by processing the electroform 50.

There is a demand for injection molding with good accuracy while achieving injection molding with high productivity by using the produced electroform 50 as it is. The inventors intensively examined injection molding using the produced electroform 50 as it is and completed the present invention.

A production method of a mold by injection molding will be described with reference to process diagrams of FIGS. 6 to 14.

Figure 6:
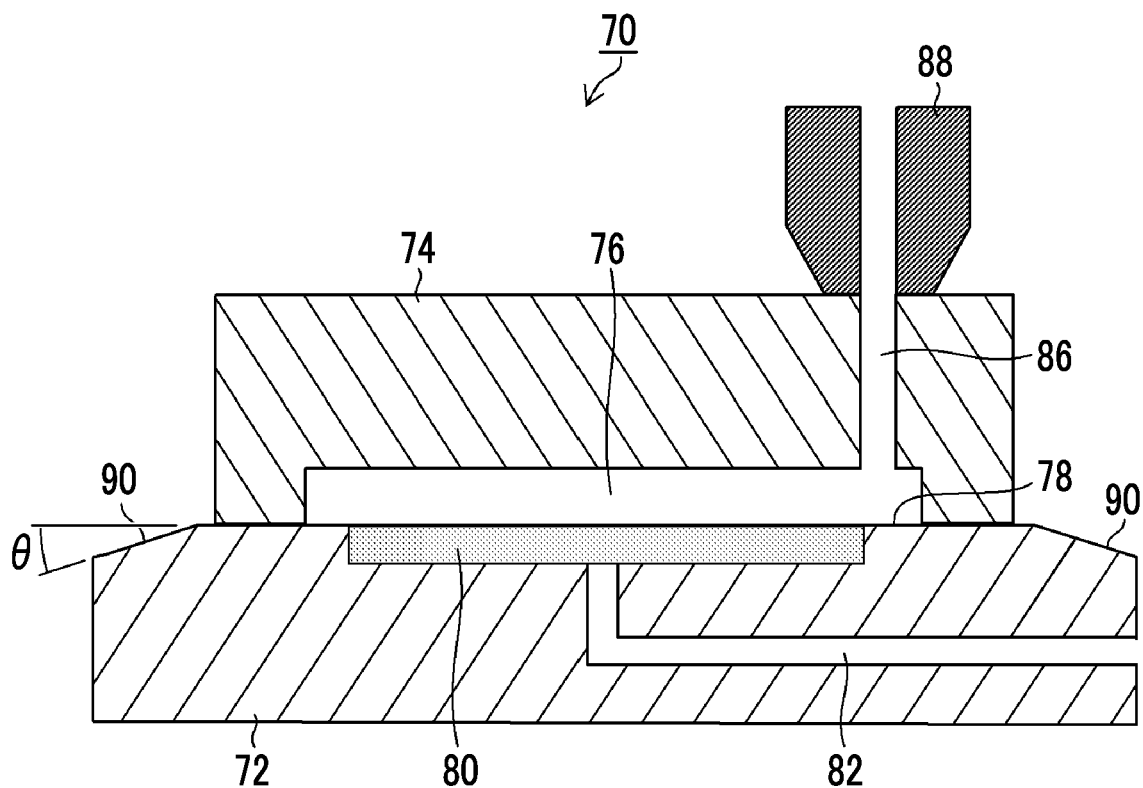
FIG. 6 is a process diagram illustrating a production method of a mold.

As illustrated in FIG. 6, a mold 70 including a first mold 72 and a second mold 74 is prepared. By clamping the first mold 72 and the second mold 74, a cavity 76 is formed inside the mold 70. The cavity 76 means a space filled with a resin.

Since the electroform 50 is fixed to the first mold 72, the side of the first mold 72 to which the electroform 50 is fixed is formed as a flat surface 78. The first mold 72 comprises an adsorption plate 80 on the flat surface 78 as a device for fixing the electroform 50. The first mold 72 comprises a suction pipe 82 in which gas communicates with the adsorption plate 80. The suction pipe 82 is connected to a vacuum pump (not illustrated). By driving the vacuum pump, air can be suctioned from the surface of the adsorption plate 80. For example, the adsorption plate 80 is formed of a porous member. Examples of the porous member include a metal sintered body, a resin, and a ceramic.

A depression 84 is formed on the cavity 76 side of the second mold 74. In this embodiment, the cavity 76 is formed by the flat surface 78 of the first mold 72 and the depression 84 (see FIG. 10) of the second mold 74, which will be described later. By configuring the first mold 72 and the second mold 74 as described above, releasing of the mold is facilitated as described later.

A gate 86 that communicates with the cavity 76 is formed in the second mold 74. The gate 86 serves as an injection port for a resin into the cavity 76 of the mold 70. The gate 86 communicates with an injection molding machine 88 that supplies the resin into the mold 70.

As illustrated in FIG. 6, the first mold 72 comprises a flank surface 90 inclined with respect to the flat surface 78 on the cavity 76 side of the first mold 72 and outside the cavity 76 formed by the first mold 72 and the second mold 74.

Figure 7:
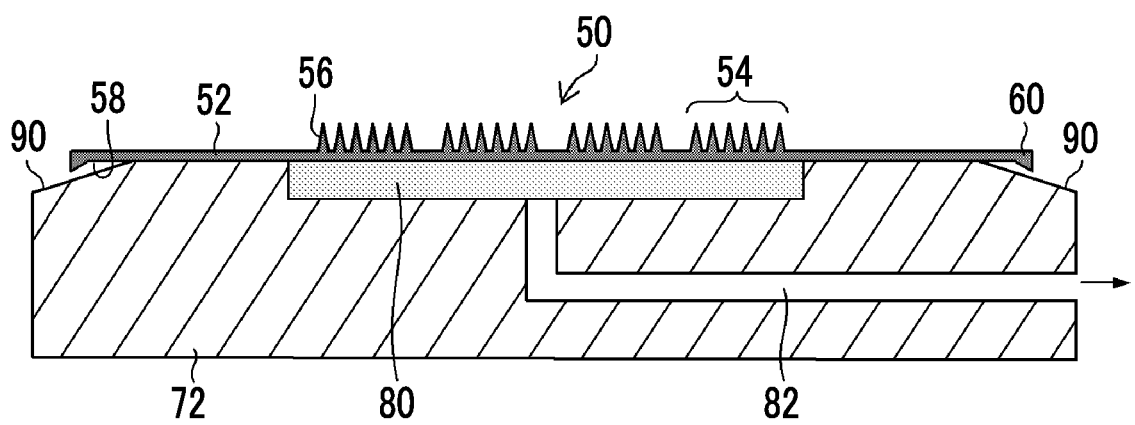
FIG. 7 is a process diagram illustrating the production method of a mold.

As illustrated in FIG. 7, the first mold 72 and the second mold 74 are opened, and the electroform 50 having the protruding patterns 54 are placed on the first mold 72. By suctioning air using the vacuum pump via the suction pipe 82, the second surface 58 of the electroform 50 is vacuum adsorbed onto the adsorption plate 80.

As illustrated in FIG. 7, since the end portion 60 of the electroform 50 is located on the flank surface 90 of the first mold 72, contact between the end portion 60 of the electroform 50 and the first mold 72 can be avoided. Therefore, it is possible to fix the electroform 50 excluding the end portion 60 of the electroform 50 to the first mold 72.

In this embodiment, the case where the electroform 50 is fixed to the first mold 72 by vacuum adsorption is exemplified, but the fixing is not limited thereto. For example, a magnet may be provided in the first mold 72 instead of the adsorption plate 80 to fix the electroform 50 to the first mold 72 using a magnetic force. Therefore, it is preferable to fix the electroform 50 to the first mold 72 by at least one of vacuum adsorption or a magnetic force.

In this embodiment, the angle θ between the flank surface 90 and the flat surface 78 is an acute angle to form the inclined surface, but the angle θ is not limited thereto. The angle θ may be a right angle or an obtuse angle as long as the contact between the end portion 60 of the electroform 50 and the first mold 72 can be avoided.

Figure 8:
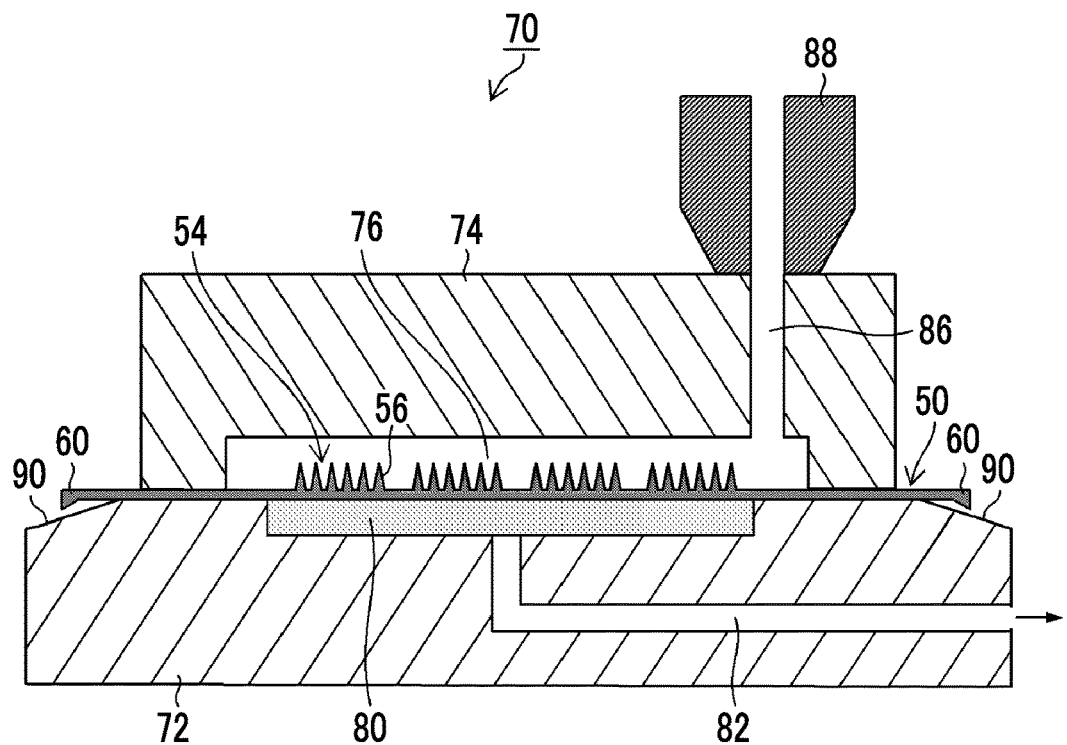
FIG. 8 is a process diagram illustrating the production method of a mold.

As illustrated in FIG. 8, in order to form the cavity 76, the first mold 72 and the second mold 74 are clamped. During the clamping, the electroform 50 excluding the end portion 60 of the electroform 50 and the region of the protruding patterns 54 is clamped between the first mold 72 and the second mold 74.

In this embodiment, the end portion 60 of the electroform 50 is not fixed to the first mold 72 due to the flank surface 90, and the end portion 60 of the electroform 50 and the region of the protruding patterns 54 are not clamped between the first mold 72 and the second mold 74.

Therefore, without processing the end portion 60 of the electroform 50, the produced electroform 50 can be fixed to the inside of the mold 70, so that it is possible to realize injection molding with high productivity. In addition, since the electroform 50 can be stably fixed to the flat surface 78 of the first mold 72, it is possible to realize injection molding with good accuracy.

The end portion 60 of the electroform 50 is a region inward of the outer edge of the electroform 50 and is a region having physical properties different from those of the other regions excluding the protruding patterns 54 of the electroform 50. In this embodiment, the end portion 60 has a larger thickness than the thickness of the other regions. In addition, the physical properties are not limited to thickness.

Figure 9:
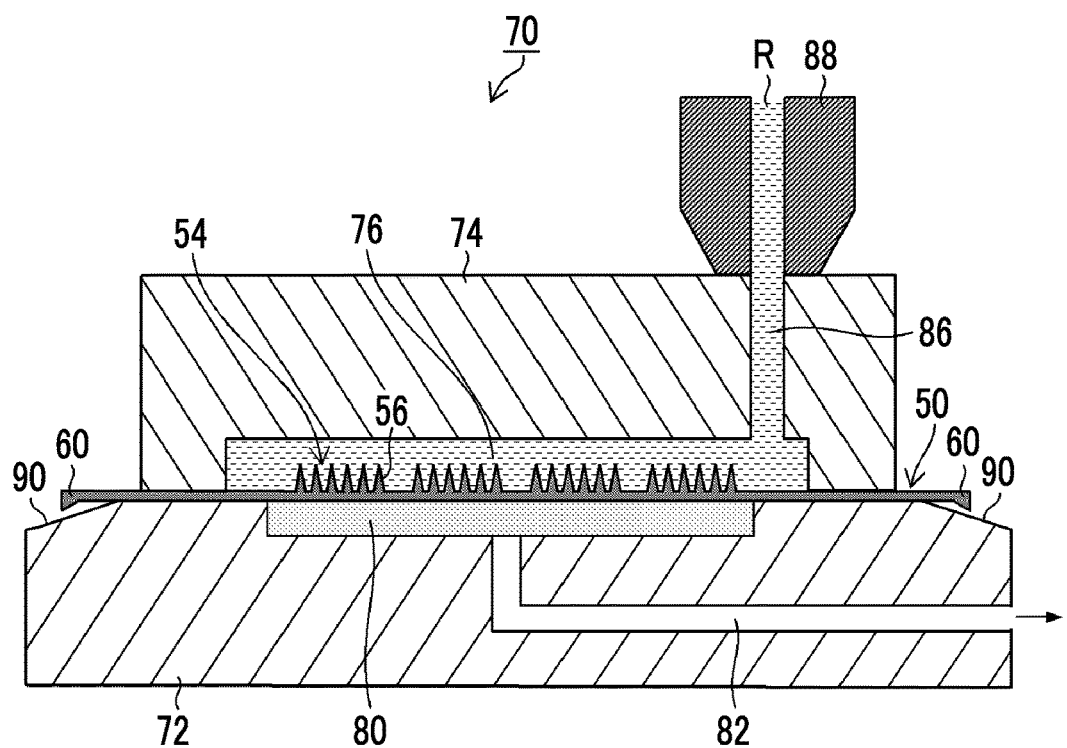
FIG. 9 is a process diagram illustrating the production method of a mold.

As illustrated in FIG. 9, a resin R is supplied from the injection molding machine 88 to the cavity 76 via the gate 86. The resin R fills the cavity 76 while passing through between the protruding patterns 54 of the electroform 50. As the resin R, a thermosetting resin or a silicone resin is preferably used, and particularly, a silicone resin is preferably used. In a case where the cavity 76 of the mold 70 is filled with the resin R, the resin R is then heated and the resin R is cured.

Figure 10:
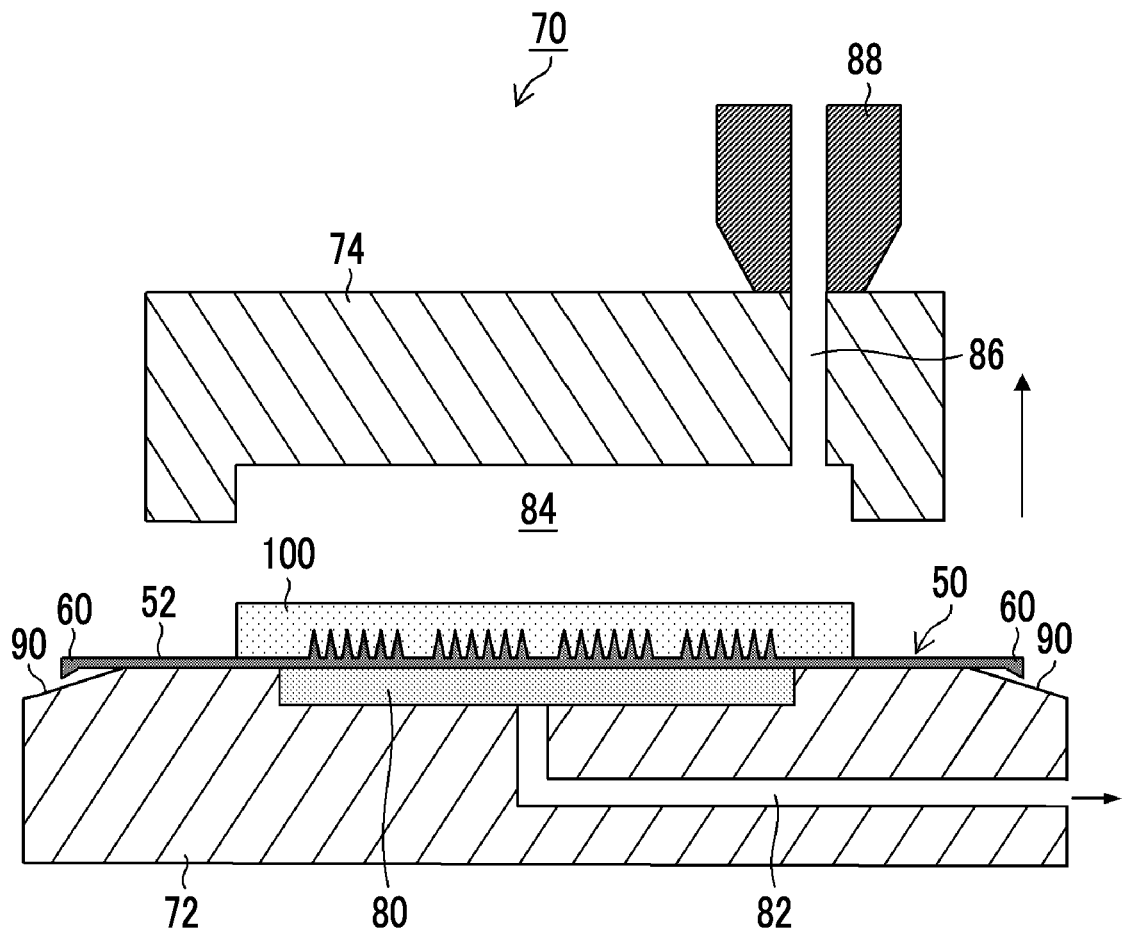
FIG. 10 is a process diagram illustrating the production method of a mold.

As illustrated in FIG. 10, in order to release the cured resin R from the electroform 50, the first mold 72 and the second mold 74 clamped are opened. During the opening, the first mold 72 and the second mold 74 are moved away from each other. As illustrated in FIG. 10, the second mold 74 has the depression 84 for forming the cavity 76. The cured resin R is a mold 100 on which recessed patterns 102

(see FIG. 14) before releasing are formed. Hereinafter, the cured resin R is sometimes referred to as the mold 100.

Figure 11:
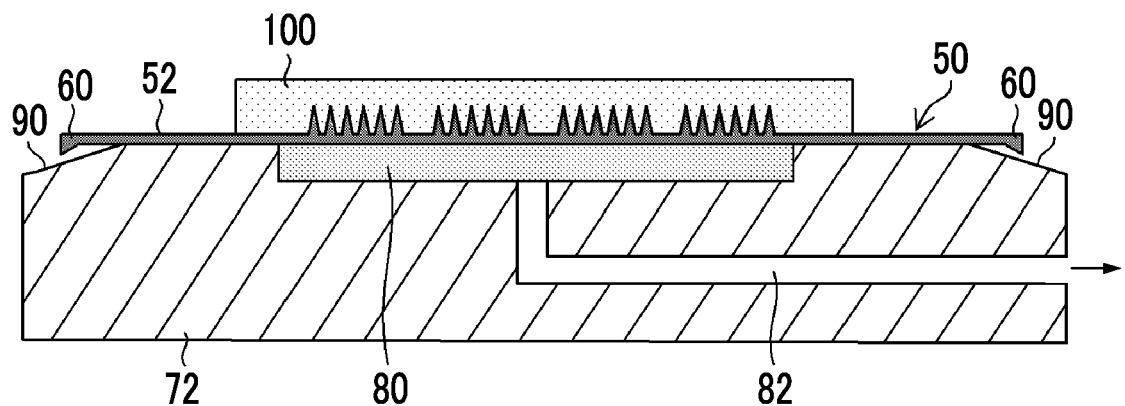
FIG. 11 is a process diagram illustrating the production method of a mold.

As illustrated in FIG. 11, the first mold 72 is separated from the second mold 74 and is moved to a stage for releasing the mold 100 from the electroform 50. In this embodiment, since the second mold 74 having the depression 84 is separated from the mold 100, the mold 100 excluding the surface being in contact with the electroform 50 fixed to the first mold 72 is exposed. Therefore, in a case where the mold 100 is released from the electroform 50, it is possible to easily release the mold 100 using the exposed surface of the mold 100.

Figure 12:
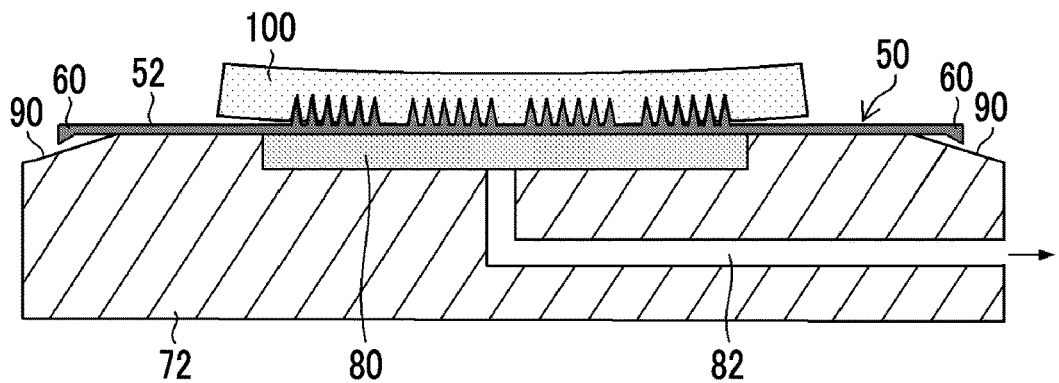
FIG. 12 is a process diagram illustrating the production method of a mold.

As illustrated in FIG. 12, the peripheral portion of the mold 100 is first separated from the electroform 50. The peripheral portion of the mold 100 may include at least two opposing sides in a case where the mold 100 is viewed in a plan view, and may include all of the four sides. The peripheral portion means a region from the outer periphery of the mold 100 to the recessed pattern 102.

Figure 13:
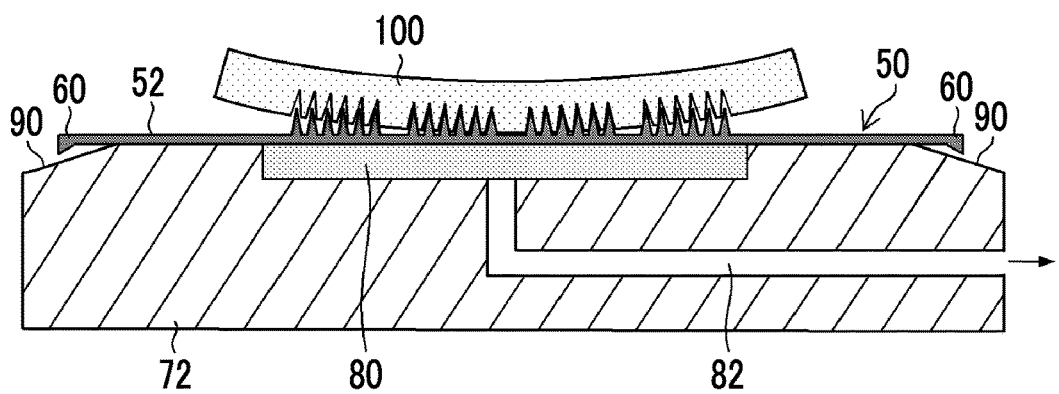
FIG. 13 is a process diagram illustrating the production method of a mold.

As illustrated in FIG. 13, the peripheral portion of the mold 100 is gradually separated from the electroform 50. In a case where the mold 100 is made of a silicone resin, since the mold 100 has elasticity, the mold 100 enters a stretched state (elastically deforms) as the peripheral portion of the mold 100 is gradually separated. As the peripheral portion of the mold 100 is further separated from the electroform 50, the elastically deformed mold 100 tries to return to its original shape, so that the mold 100 contracts. By using the contraction force of the mold 100, the mold 100 is released from the electroform 50. By using the contraction force of the mold 100 as the releasing force, no excessive force is applied between the mold 100 and the protruding patterns 54 of the electroform 50, so that it is possible to suppress failure in releasing.

Figure 14:
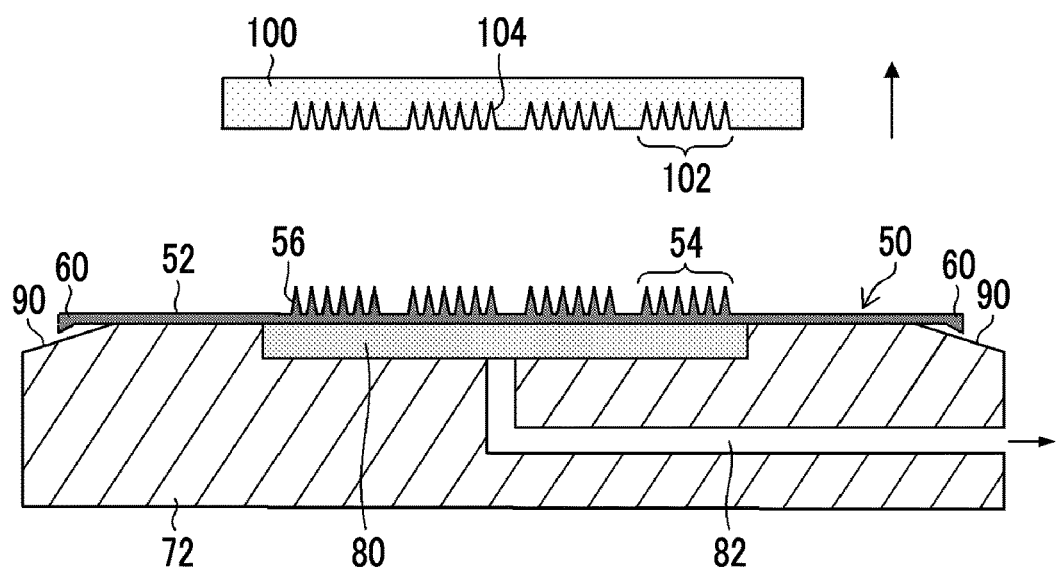
FIG. 14 is a process diagram illustrating the production method of a mold.

As illustrated in FIG. 14, finally, the mold 100 and the protruding patterns 54 of the electroform 50 are completely released from each other, and the mold 100 having the recessed patterns 102 is produced. The recessed pattern 102 is a state in which a plurality of recesses 104 are arranged in an array.

In a case where the mold 100 is repeatedly produced from the electroform 50, the protruding patterns 54 are gradually damaged, and after use about 1000 to 10,000 times, it is necessary to replace the electroform 50 with a new electroform 50. In this embodiment, by stopping the driving of the vacuum pump (not illustrated) and reducing the adsorption force of the adsorption plate 80, the electroform 50 can be replaced within a short time.

As a method of separating the peripheral portion of the mold 100 from the electroform 50, there is a method of suctioning the peripheral portion of the mold 100 in the exposed surface opposite to the surface on which the recessed patterns 102 are formed with suctioning means and separating the suctioning means from the electroform 50 while suctioning the peripheral portion.

In this embodiment, since the electroform 50 having the end portion 60 which is not processed is used, the electroform 50 which is circular in the plan view and is suitable for the electroforming treatment is preferably used for injection molding as a result.

<Manufacturing Method of Pattern Sheet>

Next, a method of manufacturing a pattern sheet using the mold 100 produced in the above-described production method will be described. FIGS. 15 to 20 are process diagrams for manufacturing a pattern sheet 110.

<Polymer Solution Supplying Step>

Figure 15:
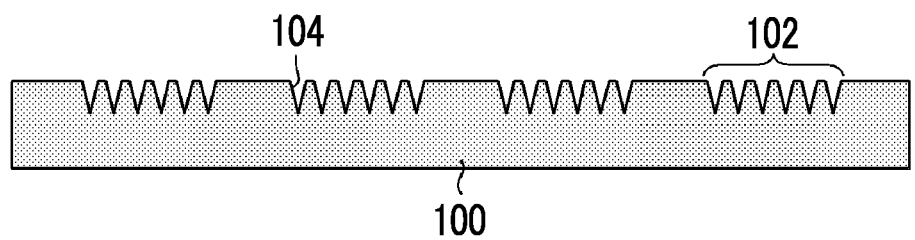
FIG. 15 is a process diagram illustrating a manufacturing method of a pattern sheet.

FIG. 15 illustrates a state in which the mold 100 is prepared. The mold 100 is manufactured by the production method of the mold described above. The mold 100 illustrated in FIG. 15 has a plurality of the recessed patterns 102. The recessed pattern 102 is a state in which a plurality of recesses 104 are arranged in an array.

Figure 16:
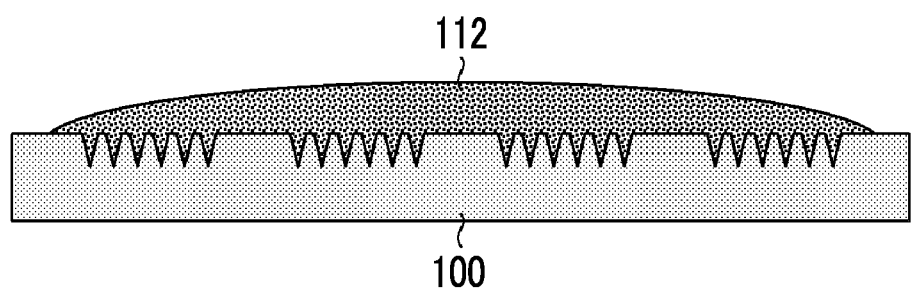
FIG. 16 is a process diagram illustrating the manufacturing method of a pattern sheet.

FIG. 16 is a view illustrating a step of supplying a polymer solution 112 to the recessed patterns 102 of the mold 100.

As the material of the polymer solution 112 forming the pattern sheet 110, it is preferable to use a water-soluble material. As a material of a resin polymer of the polymer solution 112 used to manufacture the pattern sheet 110, it is preferable to use a biocompatible resin. As such resins, sugars such as glucose, maltose, pullulan, sodium chondroitin sulfate, sodium hyaluronate, and hydroxyethyl starch, proteins such as gelatin, and biodegradable polymers such as polylactic acid and a lactic acid-glycolic acid copolymer are preferably used. In a case where the pattern sheet 110 is released from the mold 100, the pattern sheet 110 can be released using a base material (not illustrated), so that such resins can be suitably used. Although a concentration varies depending on the material, it is preferable that the concentration is set so that the resin polymer is contained at 10 to 50 mass % in the polymer solution 112 which does not contain a drug. A solvent used in the polymer solution 112 may be warm water or may be volatile, and alcohol such as ethanol or the like may be used. In addition, it is possible to dissolve the drug, which is supplied into the body according to the application, in the polymer solution 112. The polymer concentration of the polymer solution 112 containing the drug (the concentration of the polymer excluding the drug in a case where the drug itself is a polymer) is preferably 0 to 30 mass %.

As a method of preparing the polymer solution 112, in a case where a water-soluble polymer (such as gelatin) is used, a water-soluble powder may be dissolved in water and the drug may be added after the dissolution. Otherwise, a powder of a water-soluble polymer may be dissolved in a liquid in which the drug is dissolved. In a case where it is difficult to dissolve the polymer in water, heating may be performed for dissolution. The temperature can be appropriately selected depending on the kind of the polymer material, and it is preferable that heating is performed at a temperature of about 20° C. to 40° C. For the solution containing the drug, the viscosity of the polymer solution 112 is preferably 200 mPa·s or less, and more preferably 50 mPa·s or less. For a solution which does not contain a drug, the viscosity is preferably 2000 mPa·s or less, and more preferably 500 mPa·s or less. By appropriately adjusting the viscosity of the polymer solution 112, the polymer solution 112 can be easily injected into the recessed patterns 102 of the mold 100. For example, the viscosity of the polymer solution 112 can be measured with a capillary viscometer, a falling ball viscometer, a rotational viscometer, or a vibrational viscometer.

The drug to be contained in the polymer solution 112 is not particularly limited as long as the drug has a function of a drug. In particular, the drug is preferably selected from peptides, proteins, nucleic acids, polysaccharides, vaccines, pharmaceutical compounds that belong to a water-soluble low molecular weight compound, or cosmetic ingredients.

Examples of a method of injecting the polymer solution 112 into the mold 100 include application using a spin coater.

It is preferable to form a through-hole at the tip of the recess of the recessed pattern 102 of the mold 100. The air in the recess of the recessed pattern 102 can escape from the through-hole. Therefore, the polymer solution 112 can easily enter the recess of the mold 100. In addition, this step is preferably performed in a decompressed state.

Figure 17:
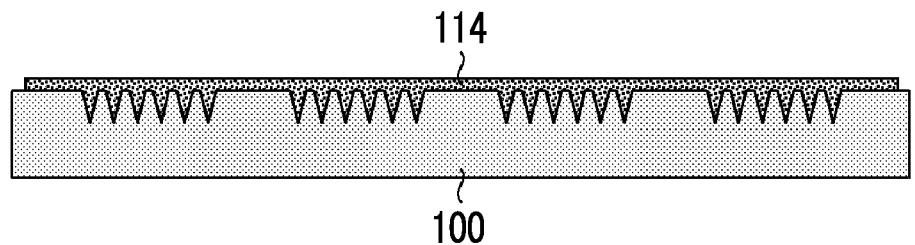
FIG. 17 is a process diagram illustrating the manufacturing method of a pattern sheet.

[Drying Step] FIG. 17 is a view illustrating a step of drying the polymer solution 112 to form a polymer sheet 114. For example, the polymer solution 112 supplied to the mold 100 can be dried by blowing air thereto. The polymer sheet 114 means a state after a desired drying treatment is applied to the polymer solution 112. The moisture content of the polymer sheet 114 and the like are appropriately set. In addition, as the moisture content of the polymer becomes too low due to the drying, it becomes difficult to peel off the polymer sheet 114. Therefore, it is preferable to keep the moisture content in a state of maintaining elasticity.

In the polymer sheet 114, a protruding pattern 116, which will be described later, which is an inverted shape of the recessed pattern 102, is formed.

Figure 18:
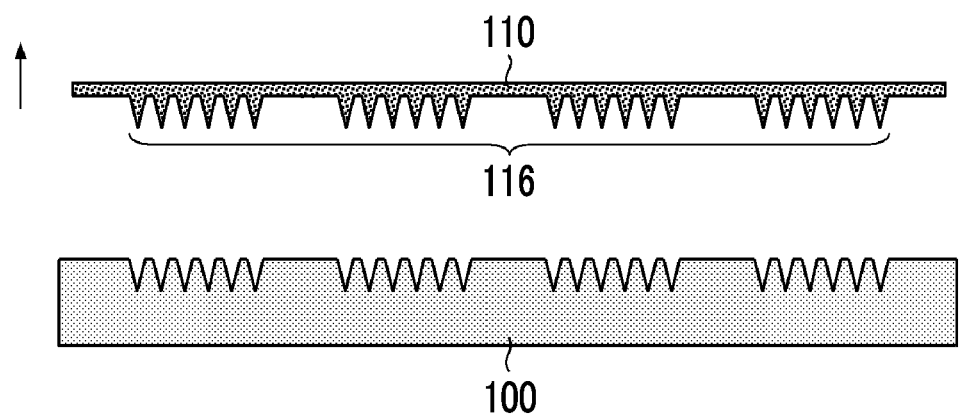
FIG. 18 is a process diagram illustrating the manufacturing method of a pattern sheet.
Figure 19:
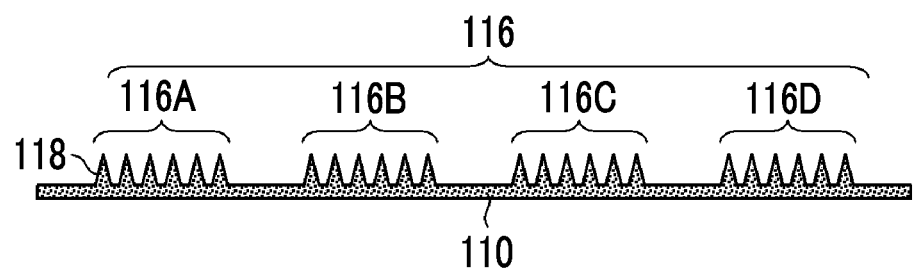
FIG. 19 is a process diagram illustrating the manufacturing method of a pattern sheet.
Figure 20:
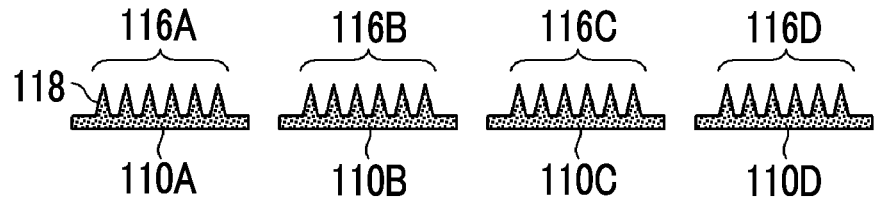
FIG. 20 is a process diagram illustrating the manufacturing method of a pattern sheet.

[Polymer Sheet Releasing Step] FIGS. 18 and 19 are views illustrating a state in which the polymer sheet 114 is released from the mold 100 to form the pattern sheet 110. FIG. 20 is a view illustrating a step of forming individual pattern sheets 110A, 110B, 110C, and 110D by cutting the pattern sheet 110.

The pattern sheet 110 released from the mold 100 is set in a cutting device (not illustrated), and the positions to cut the pattern sheet 110 are determined. Basically, the cutting position is determined for each of regions 116A, 116B, 116C, and 116D including the protruding pattern 116. As illustrated in FIG. 20, the pattern sheet 110 is cut into a plurality of individual pattern sheets 110A, 110B, 110C, and 110D.

In addition, in FIGS. 15 to 20, the method of manufacturing the pattern sheet 110 using the mold 100 has been described, but the manufacturing method is not limited thereto. For example, by joining a plurality of the molds 100, an aggregate mold in which the area of the recessed pattern 102 is increased can be produced. A pattern sheet can be manufactured using the aggregate mold.

By manufacturing the pattern sheet using the aggregate mold, the pattern sheet having a large area can be manufactured by a single manufacturing step, so that the productivity can be improved.

In this embodiment, the case where the polymer sheet 114 is formed by filling the recessed pattern 102 of the mold 100 with the polymer solution 112 and drying the resultant has been described above, but the formation of the polymer sheet 114 is not limited thereto.

For example, a polymer sheet 114 having a two-layer structure can be formed by filling the recessed pattern 102 of the mold 100 with the polymer solution 112 containing the drug, drying the resultant, thereafter filling the recessed pattern 102 of the mold 100 with the polymer solution 112 containing no drug, and drying the resultant.

In addition, there may be cases where the mold 100 is used only once and is preferably disposable. In a case where the pattern sheet 110 is used as a medicine, the pattern sheet 110 is preferably disposable in consideration of the safety of the manufactured pattern sheet 110 for the living body. By making the pattern sheet 110 disposable, there is no need to clean the mold 100, so that the cost of the cleaning can be reduced. In particular, in a case where the pattern sheet 110 is used as a medicine, high cleaning performance is required, so that the cleaning cost is high.

The protruding pattern 116 (the regions 116A, 116B, 116C, and 116D) of the manufactured pattern sheet 110 refers to a state in which a predetermined number of protrusions 118 are arranged in an array at predetermined positions. The protrusion 118 means a shape tapered toward the tip and includes a cone shape and a multistage cone shape. The multistage cone shape means a cone shape having sides at different angles from the bottom to the tip.

The height of the protrusion 118 is in a range of 0.2 mm or more and 2 mm or less, preferably 0.3 mm or more and 1.5 mm or less.

The manufactured pattern sheet 110 having the protruding pattern 116 is a duplicate of the electroform 50 having the protruding pattern 54. By setting the shape and arrangement of the protruding pattern 54 of the electroform 50 to a desired shape, the protruding pattern 116 of the manufactured pattern sheet 110 can be formed into a desired shape.

EXPLANATION OF REFERENCES

10: master model
12: first surface
14: recessed pattern
16: recess
18: second surface
20: cathode
22: shaft
24: cathode plate
26: conductive ring
30: electroforming apparatus
32: electroforming liquid
32A: electroforming liquid
34: electroforming tank
36: drain tank
38: pellet
40: titanium case
42: drain pipe
44: supply pipe
50: electroform
52: first surface
54: protruding pattern
56: protrusion
58: second surface
60: end portion
70: mold
72: first mold
74: second mold
76: cavity
78: flat surface
80: adsorption plate
82: suction pipe
84: depression
86: gate
88: injection molding machine
90: flank surface
100: mold
102: recessed pattern
104: recess
110, 110A, 110B, 110C, 110D: pattern sheet
112: polymer solution
114: polymer sheet
116: protruding pattern
116A, 116B, 116C, 116D: region
118: protrusion
R: resin
θ: angle

What is claimed is:

1. A production method of a mold having a recessed pattern, the method comprising:
    a step of preparing an electroform having a protruding pattern and a mold having a first mold and a second mold;
    a step of fixing the electroform excluding an end portion of the electroform to the first mold;
    a clamping step of clamping the first mold and the second mold to form a cavity, wherein the electroform excluding the end portion of the electroform and a region of the protruding pattern is clamped between the first mold and the second mold; and
    an injection step of filling the cavity with a resin.

2. The production method of a mold having a recessed pattern according to claim 1,
    wherein, in the step of fixing the electroform to the first mold, the electroform is fixed to the first mold by at least one of vacuum adsorption or a magnetic force.

3. The production method of a mold having a recessed pattern according to claim 1,
    wherein the resin is any one of a thermosetting resin and a silicone resin.

4. The production method of a mold having a recessed pattern according to claim 1,
    wherein the electroform has a shape in which a thickness of a region of the end portion is larger than a thickness of a region excluding the region of the end portion.

5. The production method of a mold having a recessed pattern according to claim 1, further comprising:
    after the injection step, a releasing step of curing the resin in the cavity through heating, opening the first mold and the second mold, and releasing the cured resin from the electroform.

6. The production method of a mold having a recessed pattern according to claim 1,
    wherein the electroform is circular in a plan view.

7. The production method of a mold having a recessed pattern according to claim 1,
    wherein a flat surface is formed on a side of the first mold to which the electroform is fixed, and a depression is formed on a cavity side of the second mold.

8. A manufacturing method of a pattern sheet comprising:
    a step of producing a mold having a recessed pattern by the production method of a mold having a recessed pattern according to claim 1;
    a supply step of supplying a polymer solution to the recessed pattern of the mold;
    a drying step of drying the polymer solution to form a polymer sheet; and
    a polymer sheet releasing step of releasing the polymer sheet from the mold.

9. The manufacturing method of a pattern sheet according to claim 8,
    wherein the polymer solution contains a water-soluble material.

* * * * *